United States Patent
Lin et al.

(10) Patent No.: US 11,253,380 B2
(45) Date of Patent: Feb. 22, 2022

(54) ABSORBABLE STENT

(71) Applicant: Biotyx Medical (Shenzhen) Co., Ltd, Shenzhen (CN)

(72) Inventors: Wenjiao Lin, Shenzhen (CN); Wenchao Fu, Shenzhen (CN)

(73) Assignee: Biotyx Medical (Shenzhen) Co., Ltd, Shenzhen (CN)

(*) Notice: Subject to any disclaimer, the term of this patent is extended or adjusted under 35 U.S.C. 154(b) by 112 days.

(21) Appl. No.: 16/474,226

(22) PCT Filed: Dec. 19, 2017

(86) PCT No.: PCT/CN2017/117122
§ 371 (c)(1),
(2) Date: Aug. 20, 2019

(87) PCT Pub. No.: WO2018/121340
PCT Pub. Date: Jul. 5, 2018

(65) Prior Publication Data
US 2020/0206004 A1    Jul. 2, 2020

(30) Foreign Application Priority Data
Dec. 31, 2016 (CN) .......................... 201611271031.6

(51) Int. Cl.
*A61F 2/82* (2013.01)
*A61F 2/915* (2013.01)

(52) U.S. Cl.
CPC ............... *A61F 2/915* (2013.01); *A61F 2/82* (2013.01); *A61F 2002/91541* (2013.01);
(Continued)

(58) Field of Classification Search
CPC .... A61F 2/82; A61F 2/915; A61F 2210/0004; A61F 2002/91541; A61F 2002/91575; A61F 2002/91591
See application file for complete search history.

(56) References Cited

U.S. PATENT DOCUMENTS 8,109,991 B2 * 2/2012 Clifford ................. A61F 2/91
623/1.16
9,427,344 B2   8/2016 Cottone et al.
(Continued)

FOREIGN PATENT DOCUMENTS

CN    102497970 A    6/2012
CN    204600807 U    9/2015
(Continued)

OTHER PUBLICATIONS

English Translation of CN 105902331 (original disclosed in IDS dated Jun. 27, 2019) (Year: 2016).*
(Continued)

*Primary Examiner* — Dinah Baria
(74) *Attorney, Agent, or Firm* — Maier & Maier, PLLC

(57) ABSTRACT

An absorbable stent includes an absorbable matrix. The matrix includes a number of wave-shaped rings connected by connection units and arranged in an axial direction. The wave-shaped ring includes a number of waves arranged in a circumferential direction. A peak, a valley and a support connecting the peak and the valley form the wave. Two adjacent wave-shaped rings and the connection unit form a closed side supporting unit. The matrix has a volume of [4, 40] μm per unit blood vessel area. The absorbable stent has sufficient radial supporting strength for clinical applications. Moreover, the volume of the matrix per unit blood vessel area is less than volumes of existing stents. When the absorbable stent and existing stents are made of the same material, the absorbable stent has a shorter degradation and absorption cycle.

12 Claims, 7 Drawing Sheets

(52) U.S. Cl.
CPC ............... *A61F 2002/91575* (2013.01); *A61F 2002/91591* (2013.01); *A61F 2210/0004* (2013.01)

(56) References Cited

U.S. PATENT DOCUMENTS

| | | | |
|---|---|---|---|
| 2008/0071357 A1* | 3/2008 | Girton | A61F 2/82 623/1.16 |
| 2015/0265438 A1 | 9/2015 | Hossainy et al. | |
| 2016/0081827 A1 | 3/2016 | Lumauig et al. | |
| 2016/0228267 A1 | 8/2016 | Pacetti et al. | |

FOREIGN PATENT DOCUMENTS

| | | |
|---|---|---|
| CN | 105686897 A | 6/2016 |
| CN | 105902331 A | 8/2016 |

OTHER PUBLICATIONS

International Search Report dated Feb. 12, 2018 in corresponding International application No. PCT/CN2017/117122; 2 pages.
Chinese Office Action dated Feb. 2, 2019 in corresponding application No. 201611271031.6; 11 pgs.
Indian Office Action dated Mar. 18, 2021, in connection with corresponding IN Application No. 201917030431; 5 pages.

\* cited by examiner

ABSORBABLE STENT

FIELD

The present application relates to the technical field of interventional medical devices, and more particularly relates to an absorbable stent. The absorbable stent has a relatively small absorbable matrix volume per unit vascular area and relatively high radial supporting strength.

BACKGROUND

Vascular stents may be divided into permanent stents and absorbable stents according to the length of time for remaining in blood vessels. The permanent stent is made of a non-degradable material, such as 316L stainless steel, a platinum-chromium alloy, a nickel-titanium alloy, a cobalt-chromium alloy, tantalum, titanium and the like. The long-term retention of these materials in a human body as foreign matter easily leads to hyperplasia of an intima to cause problems of intermediate and late restenosis of the blood vessel, chronic inflammation, late and extremely late thrombosis, and the like. After being implanted into the blood vessel, the absorbable stent would be gradually degraded and absorbed by an organism till it disappears, which is an ideal choice for treating cardiovascular diseases. The absorbable stent is made of a biologically absorbable material which may be an absorbable metal-based material such as a magnesium-based alloy, an iron-based alloy and a zinc-based alloy, or an absorbable polymer-based material such as polylactic acid, polycaprolactone and polycarbonate.

The corrosion and absorption cycle of the absorbable stent and the radial supporting force within the early stage of implantation, such as 3 months, are two important performance indexes. The corrosion and absorption cycle is generally required to be controlled at about 12 months, and the faster the absorption of corrosion products, the better. A thin-wall stent has become mainstream thanks to its better adherence effect after the implantation into the blood vessel and its effects of lowering the thrombosis risk through reduction in the interference with blood flow and producing a few of corrosion products.

As its corrosion rate is slow and corrosion products are difficult to absorb, an iron-based absorbable stent may not meet a clinical requirement for the corrosion and absorption cycle of an absorbable stent. The corrosion and absorption cycle may be shortened by reducing the wall thickness, which would certainly lower the radial supporting strength of the stent. The material of a stent having a relatively high corrosion rate, such as the magnesium-based absorbable stent and the polymer-based absorbable stent, is low in mechanical property. To meet the requirement for the early radial supporting strength, a relatively thick stent is required, but the thick and heavy stent would result in a large profile diameter and low bending property, is difficult to deliver, may hardly pass through a lesion locus and has all defects of a thick-wall stent.

SUMMARY

In view of this, it is necessary to provide an absorbable stent having a relatively short corrosion and absorption cycle, and the early radial supporting strength of the stent may meet clinical applications.

The present application provides an absorbable stent which includes an absorbable matrix. The absorbable matrix includes multiple turns of wave-shaped rings connected by connection units and arrayed axially. Each wave-shaped ring includes multiple circumferentially arrayed waves. Each wave includes a peak, a valley and a supporting strut connecting the peak with the valley. Two adjacent wave-shaped rings and the connection units form a closed side branch unit. The matrix volume per unit vascular area is [4, 40] μm. For a metal stent, the matrix is a bare stent. For a polymer stent, the matrix is a polymer matrix. The matrices of both the metal stent and the polymer stent do not include any coating layers or drug-loading layers. Compared with the matrix of an existing stent, the absorbable stent has a relatively small matrix volume per unit vascular area and is relatively high in radial supporting strength under the condition of using the same material.

In one embodiment, a ratio of a width of each supporting strut to a wall thickness of the matrix is [1, 2].

In one embodiment, the ratio of a width of each supporting strut to a wall thickness of the matrix is [1.45, 1.8].

In one embodiment, when a rated diameter of the matrix is [1, 5] mm, the matrix volume per unit vascular area is [4, 13] μm.

In one embodiment, when a rated diameter of the matrix is [1, 5] mm, the matrix volume per unit vascular area is [4, 7.5] μm.

In one embodiment, when a rated diameter of the matrix is [5, 15] mm, the matrix volume per unit of vascular area is [8, 25] μm.

In one embodiment, when a rated diameter of the matrix is [5, 15] mm, the matrix volume per unit of vascular area is [8, 15] μm.

In one embodiment, when a rated diameter of the matrix is [15, 40] mm, the matrix volume per unit of vascular area is [11, 40] μm.

In one embodiment, when a rated diameter of the matrix is [15, 40] mm, the matrix volume per unit of vascular area is [11, 26] μm.

In one embodiment, when the matrix is expanded to a rated diameter, a section length L of each supporting strut is [0.4, 9] mm.

In one embodiment, when the rated diameter of the matrix is [1, 5] mm, the section length L of each supporting strut is [0.5, 0.8] mm.

In one embodiment, when the rated diameter of the matrix is [5, 15] mm, the section length L of each supporting strut is [0.9, 2.0] mm.

In one embodiment, when the rated diameter of the matrix is [15, 40] mm, the section length L of each supporting strut is [1.8, 8] mm.

In one embodiment, when the matrix is expanded to a rated diameter, an included angle α of the supporting struts is [60 degrees, 120 degrees].

In one embodiment, when the matrix is expanded to the rated diameter, an included angle α of the supporting struts is [70 degrees, 100 degrees].

In one embodiment, the matrix is obtained by polishing a cut prefabricated component having a predetermined stent structure, and polishing allowances of about 0.025 to 0.060 mm are reserved in both a wall thickness direction and a strut width direction of the prefabricated component.

On the premise that the materials, patterns and specifications are the same, the wall thickness and the strut width are consistent, after the matrix is polished, the matrix volume per unit vascular area is 8 to 18 percent smaller than that of a matrix made of a prefabricated component having a small polishing allowance and a non-obvious fillet effect.

In one embodiment, a wall thickness of the matrix is 0.02 to 0.30 mm.

In one embodiment, when a rated diameter of the matrix is [1, 5] mm, the wall thickness of the matrix is [0.03 to 0.12] mm.

In one embodiment, when a rated diameter of the matrix is [5, 15] mm, the wall thickness of the matrix is [0.06 to 0.20] mm.

In one embodiment, when a rated diameter of the matrix is [15, 40] mm, the wall thickness of the matrix is [0.13 to 0.26] mm.

In one embodiment, the connection unit may be of dot shape, short strut shape, long strut shape, S shape, Ω shape and n shape.

In one embodiment, the matrix may be a magnesium-based alloy, an iron-based alloy or a zinc-shaped alloy.

The rated size is a diameter to which the stent is expected to be expanded during clinical application.

In one embodiment, the matrix may be polylactic acid, polycaprolactone or polycarbonate.

In one embodiment, the absorbable stent further includes at least one degradable polymer coating layer coated on the surface of the matrix.

In one embodiment, the degradable polymer may be degradable polyester and/or degradable polyanhydride.

In one embodiment, the degradable polyester may be any one of polylactic acid, polyglycolic acid, polylactic acid-glycollic acid, polycaprolactone, polyhydroxyalkanoate, polyacrylate, polysuccinate, poly(beta-polyhydroxybutyrate) and polyethylene glycol adipate.

In one embodiment, the degradable polyester may be a physical blend of at least two of polylactic acid, polyglycolic acid, polysuccinate, poly(beta-polyhydroxybutyrate), polycaprolactone, polyethylene glycol adipate, a polylactic acid-glycollic acid copolymer and a polyhydroxybutyrate valerate copolymer.

In one embodiment, the degradable polyester may be any one of copolymers formed by copolymerizing at least two of monomers forming the polylactic acid, the polyglycolic acid, the polysuccinate, the poly(beta-polyhydroxybutyrate), the polycaprolactone, the polyethylene glycol adipate, the polylactic acid-glycollic acid copolymer and the polyhydroxybutyrate valerate copolymer.

In one embodiment, the degradable polyanhydride may be at least one of poly-1,3-bis(p-carboxyl phenoxy)propane-sebacic acid, polyerucic acid dimer-sebacic acid or poly-fumaric acid-sebacic acid.

In one embodiment, the degradable polyanhydride may be a copolymer formed by copolymerizing at least two of monomers forming the degradable polyester or the degradable polyanhydride.

In one embodiment, the degradable polymer coating layer includes an active drug.

In one embodiment, the active drug may be at least one of a drug for inhibiting vascular proliferation, an antiplatelet drug, an antithrombotic drug, an anti-inflammatory drug or an antisensitization drug.

In one embodiment, the drug for inhibiting vascular proliferation is taxol, sirolimus and a derivative thereof.

In one embodiment, the antiplatelet drug is cilostazol.

In one embodiment, the antithrombotic drug is heparin.

In one embodiment, the anti-inflammatory drug is dexamethasone.

In the present application, by controlling the pattern design of the absorbable stent, the radial strength of the absorbable stent may meet the clinical applications and have the smaller matrix volume per unit vascular area than that of the existing stent. Therefore, compared with the existing stent, the absorbable stent of the present application has a shorter corrosion and absorption cycle under the condition of using the same stent material.

BRIEF DESCRIPTION OF THE DRAWINGS

The present application will be further described below in combination with accompanying drawings and embodiments. In the drawings.

DETAILED DESCRIPTION

To understand the technical features, objectives and effects of the present application more clearly, specific implementation modes of the present application are now described in detail in combination with the accompanying drawings.

Unless otherwise defined, all technical and scientific terms used herein are the same as meanings of general understandings of those skilled in the art of the present application. The terms used in the description of the text are merely used to describe specific exemplary embodiments, but are not intended to limit the present application.

Figure 1:
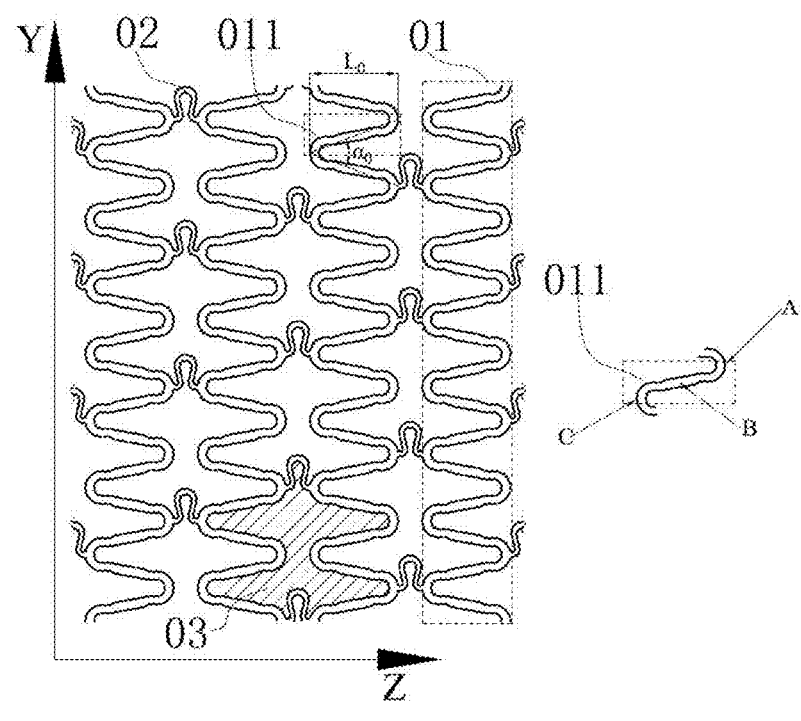
FIG. 1 is an axially spread schematic diagram of a matrix of an absorbable stent of Embodiment 1.
Figure 2:
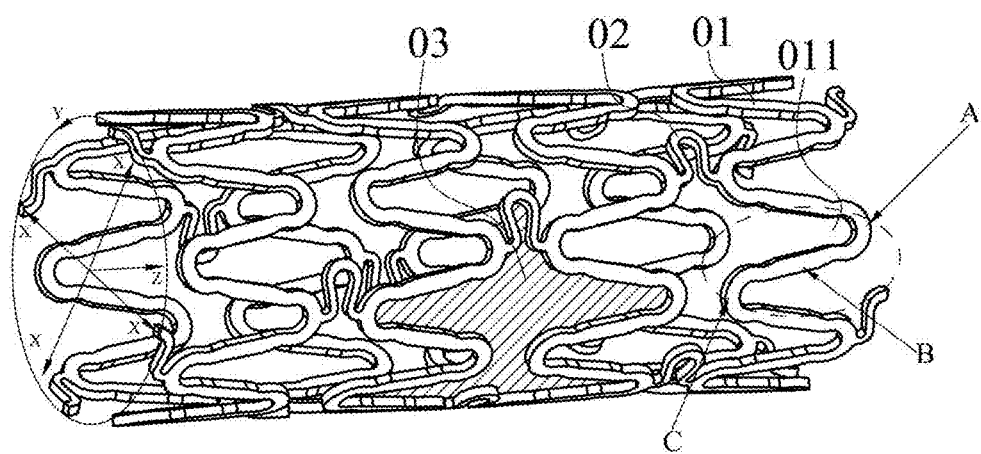
FIG. 2 is a three-dimensional structural schematic diagram of the matrix of the absorbable stent of Embodiment 1 in an original state.
Figure 3:
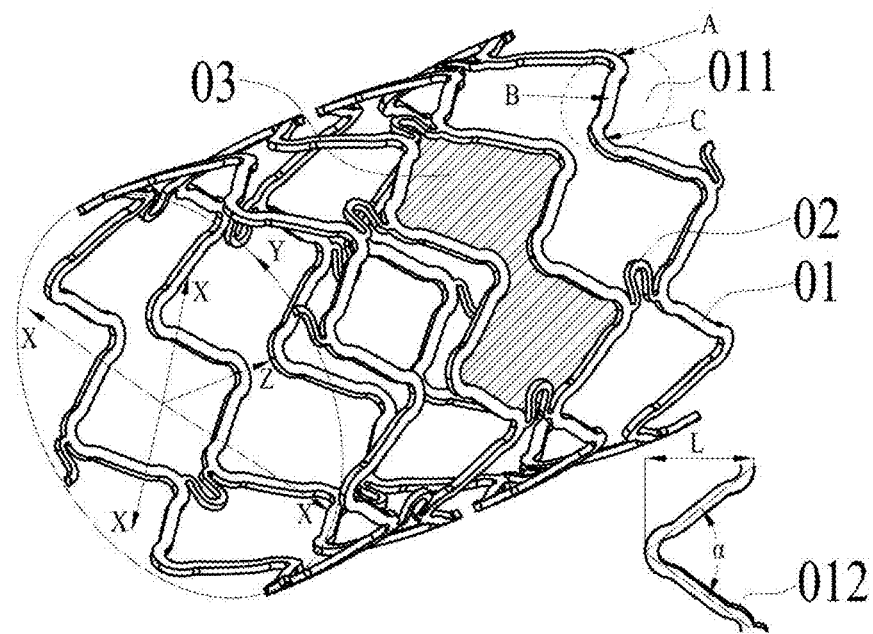
FIG. 3 is a three-dimensional structural schematic diagram of the matrix of the absorbable stent of Embodiment 1 in an expanded state.

An absorbable stent provided by the present application includes an absorbable matrix. As shown in FIG. 1, the matrix includes multiple axially arrayed wave-shaped rings. Two adjacent wave-shaped rings are connected by connection units and form a closed side branch unit together with the connection units. Each wave-shaped ring includes multiple circumferentially arrayed waves. Each wave includes a peak, a valley and a supporting strut connecting the peak with the valley. As shown in FIG. 2 and FIG. 3, the absorbable stent may be expanded from a first diameter to a second diameter. The second diameter is greater than the first diameter.

The connection unit may be a dot shape, short strut shape, long strut shape, S shape, Ω shape and n shape, as desired, and may be obtained through integrated cutting, welding or mechanical fixing.

The mechanical fixing may be hinging, pressing riveting or embedding. The extending width of the connection unit in a circumferential direction may be uniform or not uniform. For example, the connection unit is partially widened.

The corrosion and absorption cycle of the absorbable stent is related to the corrosion performance of a material of the stent matrix and the matrix volume per unit vascular area. If the material of the stent matrix is corroded slowly and the matrix volume per unit vascular area is large, the corrosion and absorption cycle of the stent is long, and otherwise, the corrosion and absorption cycle of the stent is short. When the material of the stent matrix is selected, the mechanical property and the corrosion performance of the material may be confirmed, so that factors affecting the corrosion and absorption cycle of the stent depend on the matrix volume per unit vascular area. The matrix volume per unit of vascular area may be obtained by calculating the following formula: $V=(\pi*OD*L'*A)*T/(\pi*D*L')=AT$, where V is the matrix volume per unit vascular area, D is the diameter of a blood vessel, L' is a length of the stent matrix when the stent is expanded to D, A is a coverage rate of the stent, that is, a percentage of the outer surface area of a part, which is in direct contact with the inner wall of the blood vessel, of the stent matrix which is fully expanded to a blood vessel having the diameter D to the area of a cylindrical surface where the outer surface of the stent is placed, OD is an outer diameter of the stent matrix, and T is a wall thickness of the stent. That is to say, for any blood vessels having any diameters, the matrix volume per unit vascular area depends on the coverage rate and the wall thickness of the stent when the stent is expanded to the diameter of the blood vessel. If the coverage rate and the wall thickness of the stent are smaller, the matrix volume per unit vascular area is smaller, and the corrosion and absorption cycle is shorter. The small matrix volume per unit vascular area generally indicates low radial supporting strength of the stent.

After being implanted into the blood vessel, the stent needs to bear a radial extrusion force from a lesion tissue and the blood vessel and keeps its original shape so as to achieve the effects of keeping lumen patency and maintaining unblocked blood flow in the blood vessel. Therefore, the radial supporting strength is an important performance index for guaranteeing the clinical application effectiveness of the stent, and is mainly related to the material, the pattern design and the wall thickness of the stent matrix. Under the condition that the type of the material of the stent matrix is confirmed, the radial supporting strength mainly depends on the pattern design and the wall thickness of the stent matrix. In the clinical application, the absorbable stent is often expected to have a small matrix volume per unit vascular area and high radial supporting strength.

To guarantee the clinically required radial supporting strength, the matrix volume per unit vascular area of an existing absorbable stent applied to a blood vessel having a diameter of 2 to 4 mm is generally required to be more than 19 µm. For example, the surface coverage rate A of the Absorb absorbable polylactic acid stent of the Abbott Company is 27 percent, and the wall thickness T is 156 µm, so that the matrix volume per unit vascular area is 42 µm.

Clinically, lumens having different outer diameters have different requirements for the lowest supporting strength of stents. For example, the diastolic pressure (low pressure) and the systolic pressure (high pressure) of a coronary vessel (generally with a diameter of 1 to 5 mm) of a normal person are 60 to 120 mmHg, but the systolic pressure of a hypertension patient is up to 175 mmHg, namely 23.3 kPa. In case of coronary artery spasm, the systolic pressure of the vessel is 400 mmHg, namely 55 kPa. A psychological stress state, a cold stimulation, a strenuous exercise, coronary atherosclerosis and a local stimulation to the coronary artery due to coronary angiogram as well as one-time heavy smoking or drinking may all induce the coronary artery spasm. Thus, to realize an effective support for the coronary vessel, the stent may at least bear the systolic pressure of 23.3 kPa in case of pulsation of the coronary vessel, and should bear the systolic pressure of 55 kPa in case of vasospasm. Generally, a lumen having a diameter of 1 to 5 mm should adopt a stent having the radial supporting strength of 90 kPa or more. A lumen having a diameter of 5 to 15 mm should adopt a stent having the radial supporting strength of 60 kPa or more. A lumen having a diameter of 15 mm or more should adopt a stent having the radial supporting strength of 55 kPa or more.

After some stents are implanted into blood vessels, a stent unit at a side branch is required to be fenestrated, and otherwise, the side branch may be possibly shaded and thus occluded, which leads to infarct of a cardiac muscle supported by the side branch. A lower coverage rate of the stent matrix, a greater section length of the supporting strut and an open loop design are all favorable for guaranteeing good side branch opening capacity, so that the side branch opening capacity and the radial supporting strength are a pair of contradictions. For a stent in need of fenestration on the stent unit at the side branch, its coverage rate may be neither too high nor too low because an extremely high coverage rate causes low bending performance of the stent and increased stimulation to a vascular tissue after expansion, and an extremely low coverage rate easily leads to failure in effectively opening up a lesion narrow vessel due to prolapse of a supported vascular plaque from a gap of the stent and increases the thrombus risk.

Figure 4:
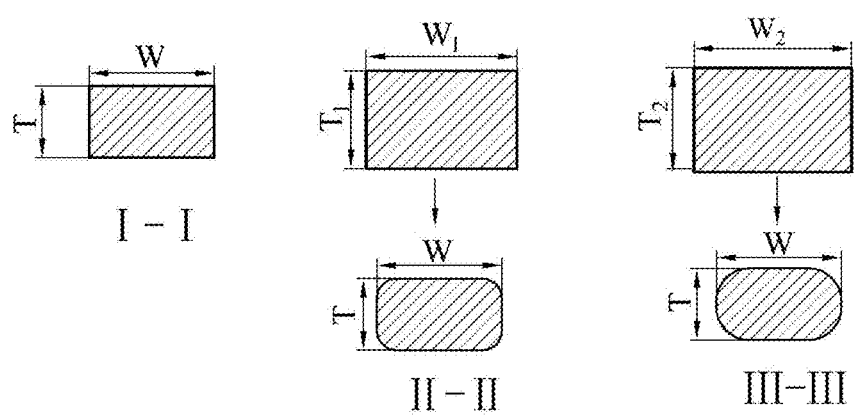
FIG. 4 is a cross sectional diagram of a supporting strut of the matrix of the absorbable stent in the present application.

Main parameters affecting the pattern design of the stent include: the number A of the wave-shaped rings, the number B of the connection units between adjacent wave-shaped rings, the number C of the waves included in the wave-shaped ring, an included angle $\alpha_0$ (namely an included angle formed by the vertex of one valley and a connecting line of the vertexes of two adjacent peaks or an included angle formed by the vertex of one peak and a connecting line of the vertexes of two adjacent valleys) of supporting struts, and the section length $L_0$ (namely a distance between the adjacent peak and valley along an axial direction Z) of the supporting strut. If the number of waves between two adjacent connection units in the circumferential direction Y is larger, the bending performance of the stent is better, and the side branch passing performance is higher. Enlargement of the included angle of the supporting struts may realize outwards expansion of the stent in a radial direction X, so that the stent may be expanded from a first diameter to a second diameter in the radial direction X. The second diameter is greater than the first diameter. The extension of the supporting strut in the circumferential direction Y is the strut width, and the extension in the radial direction X is the wall thickness; that is, the length and the width of the perpendicular cross section of the supporting strut are, respectively, the strut width and the wall thickness. As shown in FIG. 4, W is the strut width, and T is the wall thickness. The supporting strut may be of various shapes, as desired, such as an equal-width straight strut, a variable-width straight strut and an equal-width S-shaped strut. A through hole or a groove also may be formed in the supporting strut. The strut width may be uniform or changeable. The decrease of the partial strut width is favorable for reducing the absorbable matrix volume per unit vascular area, and the increase of the partial strut width contributes to improving the radial supporting strength.

The absorbable stent may be obtained by cutting a pipe into a prefabricated component having the above-mentioned predetermined stent structure and then directly polishing the prefabricated component. In addition, a fillet may be further formed on the supporting strut. The matrix volume per unit vascular area prepared by polishing the prefabricated component is 8 to 18 percent smaller than the stent volume per unit of vascular area of a matrix of a fillet effect-free absorbable stent which is made of the same material, has same patterns and is of same specification and size. The cross section of the fillet effect-free supporting strut of the absorbable stent is as shown by I-I in FIG. 4, with the wall thickness T and the strut width W. When a polishing allowance in the wall thickness direction reaches $\Delta T1$ ($\Delta T1=T1-T$), the cross section of the supporting strut of the absorbable stent is as shown by II-II in FIG. 4, thus achieving the fillet effect. When the polishing allowance in the wall thickness direction reaches $\Delta T2$ ($\Delta T2=T2-T$), the cross section of the supporting strut of the absorbable stent is as shown by in FIG. 4, and the fillet effect of this absorbable stent is more obvious than that of the cross section II-II. On the premise of same stent material, pattern and specification and unchanged sizes (the strut width and the wall thickness of the supporting strut), if the polishing allowance is larger, the fillet effect of the cross section of the supporting strut of the absorbable stent is more obvious, the absorbable matrix volume per unit vascular area is smaller, and the corrosion and absorption cycle of the absorbable stent is obviously shortened, but the radial supporting strength may not be obviously reduced as it is little affected by the fillet effect.

Figure 5:
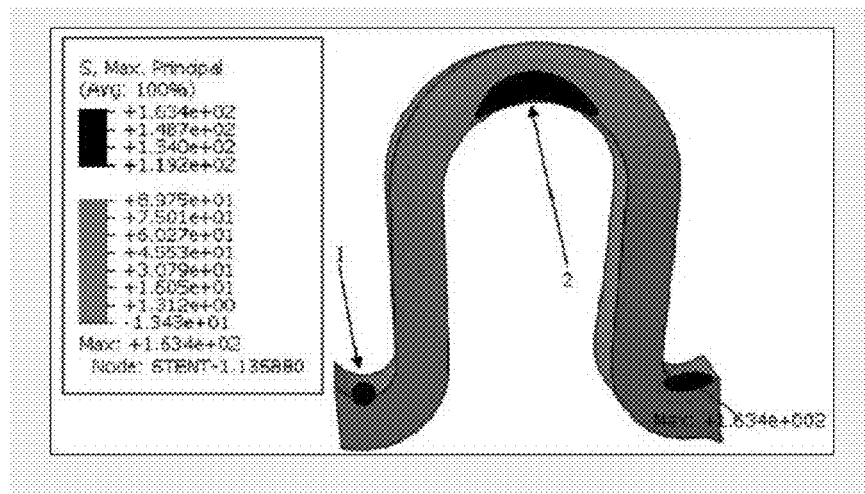
FIG. 5 is a deformation stress nephogram of connection unit 02 or 52 in the present application.
Figure 6:
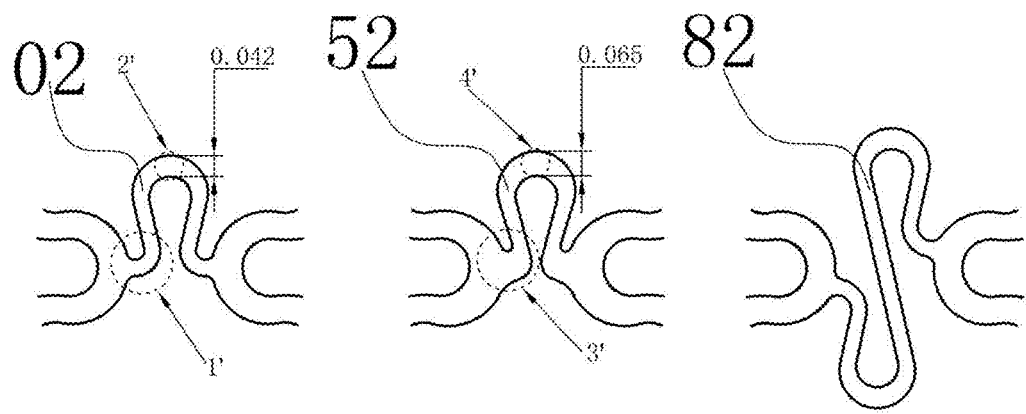
FIG. 6 is a structural schematic diagram of connection units of different sizes in the present application.

The connection unit may possibly deform non-uniformly in a radial expansion process of the stent, and has partially severely deformed positions. Each partially severely deformed position has a relatively large stress value in the radial expansion process of the stent. As shown in FIG. 5, color indicates the sizes of the stress values of all positions on the connection unit. It can be seen from FIG. 5 that the positions 1 and 2 of the connection unit have relatively large stress values, which indicates that the positions 1 and 2 deform severely. Widening the partially severely deformed positions contributes to improving the radial supporting strength of the stent. As shown in FIG. 6, the connection units 02 and 52 are of similar shapes, but the partially severely deformed positions 3' and 4' of the connection unit 52 are wider than the partially severely deformed positions 1' and 2' of the connection unit 02 and have larger extensions in the circumferential direction. In case that other factors (the material, the design of the supporting strut, the wall thickness and the like) are confirmed, a stent with the connection unit 52 has higher radial supporting strength than a stent with the connection unit 02.

The matrix volume per unit vascular area is tested by adopting, for example, Micro CT equipment produced by the BRUKER Company through the following method of expanding the matrix to its rated diameter D', then fully scanning the stent by adopting the Micro CT to obtain a three-dimensional model of the stent at this moment, performing volumetric integration on the three-dimensional model to obtain the volume of the matrix, and dividing the volume by the area of a vascular cylindrical surface where the outer surface of the matrix is placed at this moment to obtain the matrix volume per unit lumen V. The area S of the blood vessel where the outer surface of the matrix is placed is obtained by calculating the following formula: $S=\pi*D'*L'$ where D' is the rated diameter of the stent and L' is the length of the stent at this moment. The radial supporting strength is tested by adopting a radial supporting force tester produced by the MSI Company through the following method of expanding the stent to its rated diameter D', putting it into the radial supporting force tester to enable the stent to be compressed to deform under the action of a pressure head and measuring pressure/KPa on the stent when the diameter of the stent is decreased to a certain value in a radial compression process (simulated actual stress state of the stent in the vessel). The diameter decrease amount herein is defined to be 10 percent of the rated diameter of the stent, namely it is the pressure/KPa on the stent when the stent is compressed from the rated diameter to 90 percent of the rated diameter.

The bending performance is evaluated through a three-point bending experiment of the stent. The three-point bending experiment is performed on a universal mechanical test machine produced by the MTS Company through the following method of crimping the stent on a delivery for three-point bending test and performing the three-point bending test according to the standard YY/T0858-2011 to obtain a maximum three-point bending resistance value. If the three-point bending resistance is lower, the bending performance of the stent is better.

The side branch passing performance is evaluated through a theoretical limit-expansion diameter OD' of the side branch unit. The theoretical limit-expansion diameter OD' is equal to $C/\pi$, and C is the perimeter of the edge of the inner side of the side branch unit (03 in FIG. 1).

The nominal pressure is a pressure clinically required for completely expanding the stent. Complete expansion is a state that the stent is expanded to be matched with the diameter of its application lumen.

The rated diameter is a diameter of a completely expanded stent under the nominal pressure. The rated diameter of the stent is matched with the diameter of its application lumen.

Additionally, when the absorbable stent further includes a coating layer, such as a polymer coating layer or a drug-loading coating layer, located on the surface of the matrix, the coating layer is required to be removed before the above-mentioned test, and only the matrix of the absorbable stent is tested.

The absorbable stent of the present application may be a coronary vessel stent, a cerebrovascular stent, a peripheral vascular stent, a biliary stent, an esophageal stent and/or a urethral stent. The present application is further described below in detail in combination with specific embodiments by taking an iron-based alloy coronary stent and a peripheral stent for example, but the scope of the present application is not limited to these stents.

Embodiment 1

Referring to FIGS. 1 to 3 together, an absorbable coronary vessel stent is provided. A matrix is made of nitrided iron, and includes multiple turns of wave-shaped rings 01 connected through connection units 02 and arrayed axially. Two adjacent wave-shaped rings 01 and the connection unit 02 form a closed side branch unit 03. Each wave-shaped ring 01 includes multiple circumferentially arrayed waves 011. Each wave 011 includes peak A, valley C, and supporting strut B connecting the peak A with the valley C.

A prefabricated component, which is obtained by cutting a nitrided iron tube having an outer diameter of 1.3 mm and has a predetermined matrix structure, has a polishing allowance of 0.025 mm. After the prefabricated component is polished into the absorbable stent 100, the supporting strut B of the stent 100 has a wall thickness of 0.038 mm and a uniform strut width of 0.076 mm. A ratio of the strut width to the wall thickness of the supporting strut B is 2.0. The number A of the wave-shaped rings 01 is 28. The number B of the connection units 02 between the adjacent wave-shaped rings 01 is 3. The number C of the waves 011 included in the wave-shaped rings 01 is 12. The included angle α 0 of the supporting struts B is 56 degrees. The section length L0 of the supporting strut B is 0.640 mm.

When the stent is implanted into a lumen of 2.0 mm, the included angle α of the supporting struts B is 92 degrees, the section length L of the supporting strut B is 0.506 mm, and the absorbable matrix volume per unit vascular area is 4.0 μm.

The radial supporting strength of the absorbable coronary vessel stent is 90 KPa, the maximum three-point bending resistance is 0.30 N, and the theoretical limit-expansion diameter of the side supporting unit is 2.10 mm, so that the radial supporting strength of the absorbable coronary vessel stent may meet the clinical applications and have good bending performance and side branch passing performance.

Embodiment 2

Figure 7:
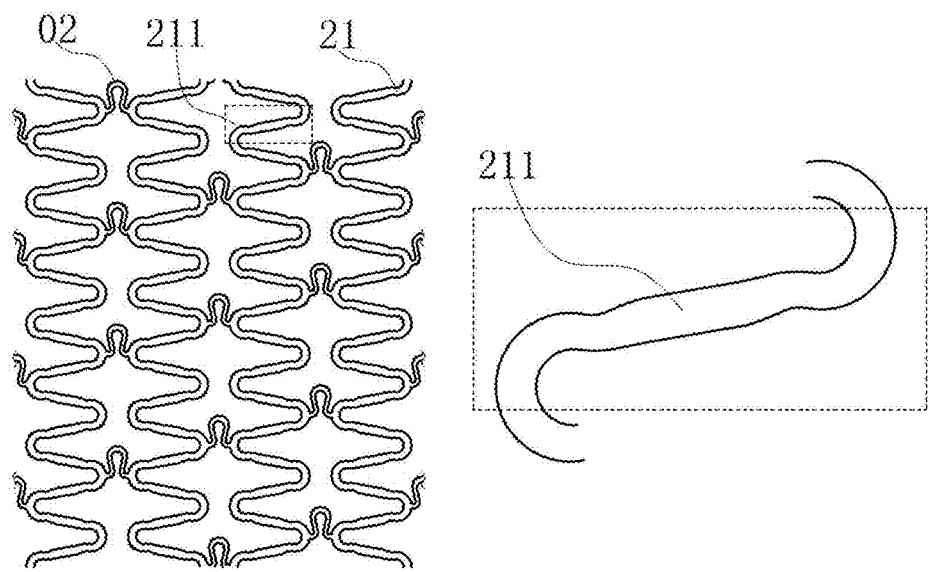
FIG. 7 is a pattern design schematic diagram of a matrix of an absorbable stent in Embodiment 2.

Referring to FIG. 7, a matrix of an absorbable coronary vessel stent of the present embodiment is made of nitrided iron, and has a similar structure to that of the matrix of the absorbable coronary vessel stent of Embodiment 1. A difference lies in that:

a prefabricated component is obtained by cutting a nitrided iron tube having an outer diameter of 1.6 mm and has a predetermined matrix structure has a polishing allowance of 0.030 mm. After the prefabricated component is polished into the absorbable stent 200, the supporting strut of the stent has a wall thickness of 0.052 mm, wave 211 are as shown in FIG. 7, and a strut width varies within [0.074, 0.091] mm.

A ratio of the strut width of the supporting strut to the wall thickness is [1.42, 1.75]. The number A of the wave-shaped rings is 15. The number B of the connection units between the adjacent wave-shaped rings is 4. The number C of the waves included in the wave-shaped ring is 16. The included angle α0 of the supporting struts is 41.5 degrees. The section length L0 of the supporting strut is 0.829 mm.

When the stent is implanted into a lumen of 3.0 mm, the included angle α of the supporting struts is 83 degrees, the section length L of the supporting strut is 0.667 mm, and the absorbable matrix volume per unit vascular area is 6.9 μm.

The radial supporting strength of the absorbable coronary vessel stent is 120 KPa, the maximum three-point bending resistance is 0.35 N, and the theoretical limit-expansion diameter of the side branch unit is 2.70 mm, so that the radial supporting strength of the absorbable coronary vessel stent may meet the clinical applications and have good bending performance and side branch passing performance.

Embodiment 3

A matrix of an absorbable coronary vessel stent of the present embodiment is made of nitrided iron, and has a similar structure to that of the matrix of the absorbable coronary vessel stent of Embodiment 2. A difference lies in that: the structure of each connection unit 52 of the stent is as shown in FIG. 6, and the wall thickness of each supporting strut of the stent is reduced to 0.047 mm.

When the stent is implanted into a lumen of 3.0 mm, the radial supporting strength of the absorbable coronary vessel stent is 120 KPa, which is kept consistent with that of the absorbable coronary vessel stent in Embodiment 2, but the absorbable matrix volume per unit vascular area of the absorbable coronary vessel stent is smaller, which is 6.4 μm.

Embodiment 4

Figure 11:
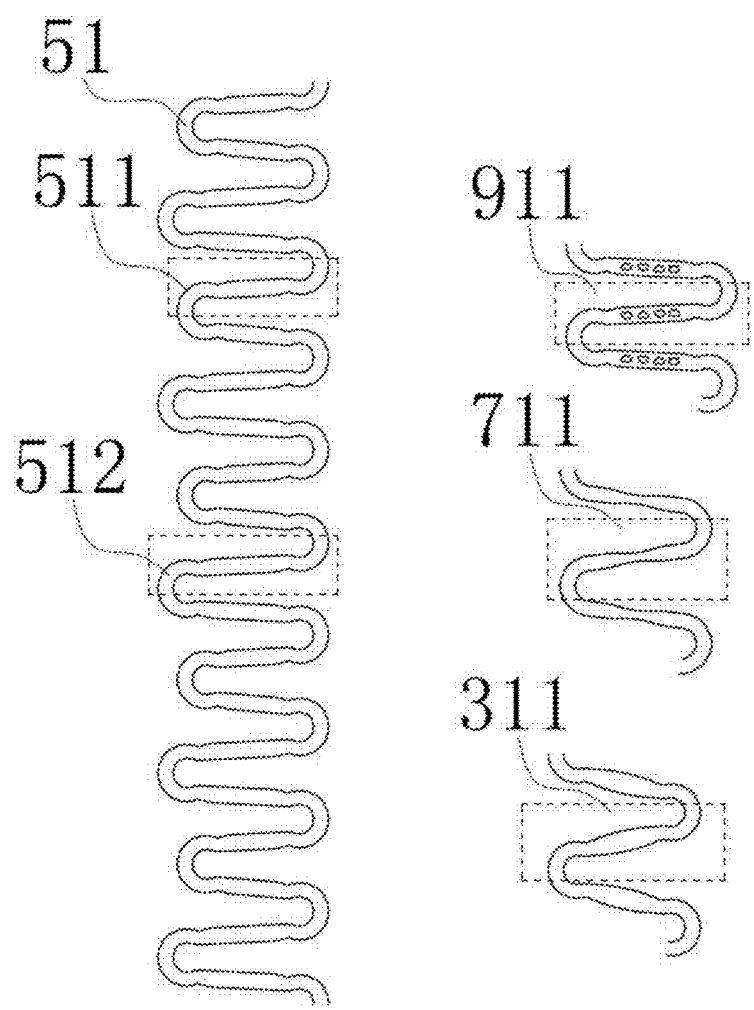
FIG. 11 is a wave or pattern design schematic diagram of the matrixes of the absorbable stents in different embodiments of the present application.

Referring to FIG. 11, a matrix of an absorbable coronary vessel stent of the present embodiment is made of nitrided iron, and has a similar structure to that of the matrix of the absorbable coronary vessel stent of Embodiment 1. A difference lies in that:

a prefabricated component is obtained by cutting a nitrided iron tube having an outer diameter of 1.6 mm and has a predetermined matrix structure has a polishing allowance of 0.040 mm. After the prefabricated component is polished into the absorbable stent 300, the supporting strut of the stent has a wall thickness of 0.052 mm, and the structure of wave 311 is as shown in FIG. 11. The supporting strut is partially widened, and has a strut width of [0.091, 0.104] mm. A ratio of the strut width to the wall thickness of the supporting strut is [1.75, 2.00]. The number A of the wave-shaped rings is 15. The number B of the connection units between the adjacent wave-shaped rings is 4. The number C of the waves included in the wave-shaped ring is 16. The included angle α0 of the supporting struts is 41 degrees. The section length L0 of the supporting strut is 0.840 mm.

When the stent is implanted into a lumen of 3.0 mm, the included angle α of the supporting struts is 82 degrees, the section length L of the supporting strut is 0.678 mm, and the absorbable matrix volume per unit vascular area is 7.0 μm.

The radial supporting strength of the absorbable coronary vessel stent is 140 KPa, the maximum three-point bending resistance is 0.50 N, and the theoretical limit-expansion diameter of the side branch unit is 2.45 mm, so that the radial supporting strength of the absorbable coronary vessel stent may meet the clinical applications and have good bending performance and side branch passing performance.

Embodiment 5

Figure 8:
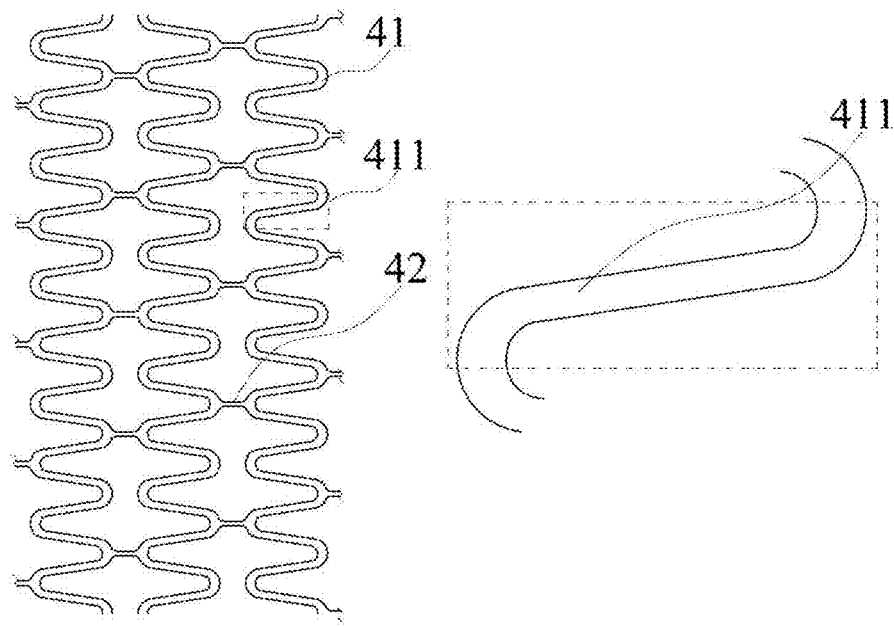
FIG. 8 is a pattern design schematic diagram of a matrix of an absorbable stent in Embodiment 5.

Referring to FIG. 8, a matrix of an absorbable coronary vessel stent of the present embodiment is made of nitrided iron, and has a similar structure to that of the matrix of the absorbable coronary vessel stent of Embodiment 1. A difference lies in that:

a prefabricated component is obtained by cutting a nitrided iron tube having an outer diameter of 1.6 mm and has a predetermined matrix structure has a polishing allowance of 0.030 mm. After the prefabricated component is polished into the absorbable stent 400, the supporting strut of the stent has a wall thickness of 0.055 mm, wave 411 are as shown in FIG. 8, and the strut width varies within [0.056, 0.069] mm.

A ratio of the strut width to the wall thickness of the supporting strut is [1.02, 1.25]. The number A of the wave-shaped rings is 17. The number B of the connection units between the adjacent wave-shaped rings is 5. The number C of the waves included in the wave-shaped ring is 20. The included angle α0 of the supporting struts is 40 degrees. The section length L0 of the supporting strut is 0.691 mm.

When the stent is implanted into a lumen of 3.0 mm, the included angle α of the supporting struts is 80 degrees, the section length L of the supporting strut is 0.562 mm, and the absorbable matrix volume per unit vascular area is 6.5 µm.

The radial supporting strength of the absorbable coronary vessel stent is 120 KPa, the maximum three-point bending resistance is 0.40 N, and the theoretical limit-expansion diameter of the side branch unit is 2.25 mm, so that the radial supporting strength of the absorbable coronary vessel stent may meet the clinical applications and have good bending performance and side branch passing performance.

Embodiment 6

Referring to FIG. 11, a matrix of an absorbable peripheral vascular stent of the present embodiment is made of nitrided iron, and has a similar structure to that of the matrix of the absorbable coronary vessel stent of Embodiment 1. A difference lies in that: the structure of each wave-shaped ring 51 of the absorbable peripheral vascular stent is as shown in FIG. 11, and the structure of each connection unit 52 is as shown in FIG. 6. The partially severely deformed positions 3' and 4' are wider in size and have larger extensions in the circumferential direction.

A prefabricated component is obtained by cutting a nitrided iron tube having an outer diameter of 1.5 mm, and has a predetermined matrix structure, has a polishing allowance of 0.035 mm. After the prefabricated component is polished into the absorbable stent 500, the supporting strut of the stent has a wall thickness of 0.065 mm, and the structure of waves is as shown by 511 and 512 in FIG. 11.

The supporting strut has a uniform strut width of 0.094 mm. A ratio of the strut width to the wall thickness is 1.45. The number A of the wave-shaped rings is 22. The number B of the connection units between the adjacent wave-shaped rings is 5. The number C of the waves included in the wave-shaped ring is 20. The included angle α0 of the supporting struts in the wave 511 is 35 degrees, and the section length L0 is 0.747 mm. The included angle α0 of the supporting struts in the wave 512 is 30 degrees, and the section length L0 is 0.879 mm.

When the stent is implanted into a lumen of 3.5 mm, the included angle α of the supporting struts in the wave 511 is 90 degrees, and the section length L is 0.550 mm; the included angle α of the supporting struts in the wave 512 is 74 degrees, and the section length L is 0.730 mm; and the absorbable matrix volume per unit vascular area of the absorbable stent is 9.0 µm.

The radial supporting strength of the absorbable peripheral vascular stent is 110 KPa, the maximum three-point bending resistance is 0.60 N, and the theoretical limit-expansion diameter of the side branch unit is 2.55 mm, so that the radial supporting strength of the peripheral vascular stent may meet the clinical applications and have good bending performance and side branch passing performance.

Embodiment 7

Figure 9:
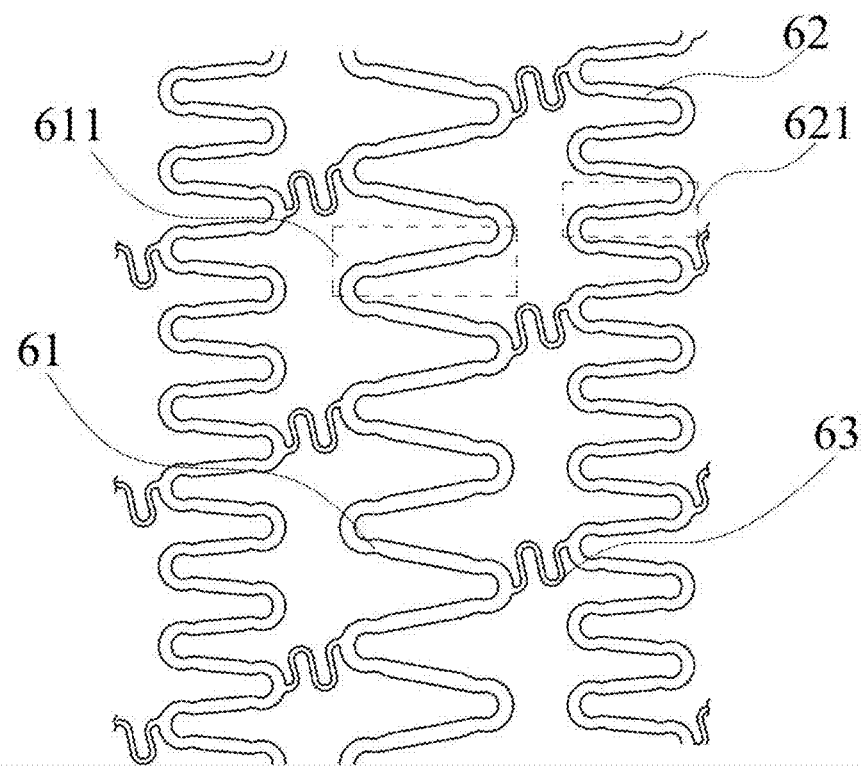
FIG. 9 is a pattern design schematic diagram of a matrix of an absorbable stent in Embodiment 7.

Referring to FIG. 9, a matrix of an absorbable peripheral vascular stent of the present embodiment is made of nitrided iron, and has a similar structure to that of the matrix of the absorbable coronary vessel stent of Embodiment 1. A difference lies in that: the structures of wave-shaped rings of the stent are as shown by 61 and 62, and the structure of each connection unit is as shown by 63. A prefabricated component is obtained by cutting a nitrided iron tube having an outer diameter of 1.5 mm and has a predetermined matrix structure has a polishing allowance of 0.035 mm. After the prefabricated component is polished into the absorbable stent 600, the supporting strut in the stent has a wall thickness of 0.065 mm, and the structures of waves are as shown by 611 and 621 in FIG. 9. The supporting strut in the wave 611 has a uniform strut width of 0.094 mm, and a ratio of the strut width to the wall thickness is 1.45. The supporting strut in the wave 621 has a uniform strut width of 0.104 mm, and a ratio of the strut width to the wall thickness is 1.60.

Design parameters of the wave-shaped rings 61 are as follows: the number A of the wave-shaped rings is 18, the number B of the connection units between the adjacent wave-shaped rings is 3, the number C of the waves included in the wave-shaped ring is 12; and the included angle α0 of the supporting struts in the wave 611 is 28 degrees, and the section length L0 is 0.788 mm. Design parameters of the wave-shaped rings 62 are as follows: the number A of the wave-shaped rings is 18, the number B of the connection units between the adjacent wave-shaped rings is 3, the number C of the waves included in the wave-shaped ring is 18; and the included angle α0 of the supporting struts in the wave 621 is 22 degrees, and the section length L0 is 0.673 mm.

When the stent is implanted into a lumen of 4.5 mm, the included angle α of the supporting struts in the wave 611 is 93 degrees, and the section length L is 0.559 mm; the included angle α of the supporting struts in the wave 621 is 70 degrees, and the section length L is 0.561 mm; and the absorbable matrix volume per unit vascular area of the absorbable peripheral vascular stent is 10 µm.

The radial supporting strength of the absorbable peripheral vascular stent is 105 KPa, the maximum three-point bending resistance is 0.80 N, and the theoretical limit-expansion diameter of the side branch unit is 2.34 mm, so that the radial supporting strength of the absorbable peripheral vascular stent may meet the clinical applications and have good bending performance and side branch passing performance.

Embodiment 8

Referring to FIG. 11, a matrix of an absorbable peripheral vascular stent of the present embodiment is made of low-carbon steel, and has a similar structure to that of the matrix of the absorbable coronary vessel stent of Embodiment 1. A difference lies in that:

a prefabricated component is obtained by cutting a low-carbon steel tube having an outer diameter of 1.8 mm and has a predetermined matrix structure has a polishing allowance of 0.035 mm. After the prefabricated component is polished into the absorbable stent 700, the supporting strut of the stent has a wall thickness of 0.082 mm. The structure of wave 711 is as shown in FIG. 11. The supporting strut is partially narrowed and has a strut width of [0.123, 0.135] mm. A ratio of the strut width to the wall thickness of the supporting strut is [1.50, 1.65].

The number A of the wave-shaped rings is 36. The number B of the connection units between the adjacent wave-shaped rings is 3. The number C of the waves included in the wave-shaped ring is 18. The included angle α0 of the supporting struts is 31 degrees. The section length L0 of the supporting strut is 1.133 mm.

When the stent is implanted into a lumen of 4.75 mm, the included angle α of the supporting struts is 90 degrees, the section length L of the supporting strut is 0.829 mm, and the absorbable matrix volume per unit vascular area of the absorbable stent is 13.0 µm.

The radial supporting strength of the absorbable peripheral vascular stent is 100 KPa, the maximum three-point bending resistance is 1.30 N, and the theoretical limit-expansion diameter of the side branch unit is 3.13 mm, so that the radial supporting strength of the absorbable peripheral vascular stent may meet the clinical applications and have good bending performance and side branch passing performance.

Embodiment 9

A matrix of an absorbable peripheral vascular stent of the present embodiment is made of nitrided iron, and has a similar structure to that of the matrix of the absorbable coronary vessel stent of Embodiment 1. A difference lies in that: the structure of each connection unit 82 of the stent is as shown in FIG. 6.

A prefabricated component is obtained by cutting a nitrided iron tube having an outer diameter of 2.1 mm and has a predetermined matrix structure has a polishing allowance of 0.045 mm. After the prefabricated component is polished into the absorbable stent 800, the supporting strut of the stent has a wall thickness of 0.086 mm. The structure of each wave is similar to that of the wave 011 of the absorbable stent of Embodiment 1. The uniform strut width is 0.155 mm. A ratio of the strut width to the wall thickness of the supporting strut is 1.8.

The number A of the wave-shaped rings is 18. The number B of the connection units between the adjacent wave-shaped rings is 5. The number C of the waves included in the wave-shaped ring is 20. The included angle α0 of the supporting struts is 27 degrees. The section length L0 of the supporting strut is 1.374 mm.

When the stent is implanted into a lumen of 6.0 mm, the included angle α of the supporting struts is 84 degrees, the section length L of the supporting strut is 1.047 mm, and the absorbable matrix volume per unit vascular area of the absorbable peripheral vascular stent is 8.6 µm.

The radial supporting strength of the absorbable peripheral vascular stent is 90 KPa, the maximum three-point bending resistance is 1.71 N, and the theoretical limit-expansion diameter of the side branch unit is 3.84 mm, so that the absorbable peripheral vascular stent may meet the clinical applications and have good bending performance and side branch passing performance.

Embodiment 10

Referring to FIG. 11, a matrix of an absorbable peripheral vascular stent of the present embodiment is made of pure iron, and has a similar structure to that of the matrix of the absorbable coronary vessel stent of Embodiment 1. A difference lies in that:

a prefabricated component is obtained by cutting a pure iron tube having an outer diameter of 4.2 mm and has a predetermined matrix structure has a polishing allowance of 0.050 mm. After the prefabricated component is polished into the absorbable stent 900, the supporting strut of the stent has a wall thickness of 0.160 mm. The structure of the supporting strut is as shown by 911 in FIG. 11. A through hole is formed in the supporting strut. The supporting strut has a uniform strut width of 0.232 mm.

A ratio of the strut width to the wall thickness of the supporting strut is 1.45. The number A of the wave-shaped rings is 13. The number B of the connection units between the adjacent wave-shaped rings is 6. The number C of the waves included in the wave-shaped ring is 24. The included angle α0 of the supporting struts is 28 degrees. The section length L0 of the supporting strut is 2.205 mm.

When the stent is implanted into a lumen of 12.0 mm, the included angle α of the supporting struts is 87.5 degrees, the section length L of the supporting strut is 1.641 mm, and the absorbable matrix volume per unit vascular area of the absorbable stent is 13.3 µm.

The radial supporting strength of the absorbable peripheral vascular stent is 65 KPa, the maximum three-point bending resistance is 2.10 N, and the theoretical limit-expansion diameter of the side branch unit is 5.93 mm, so that the radial supporting strength of the absorbable peripheral vascular stent may meet the clinical applications and have good bending performance and side branch passing performance.

Embodiment 11

Figure 10:
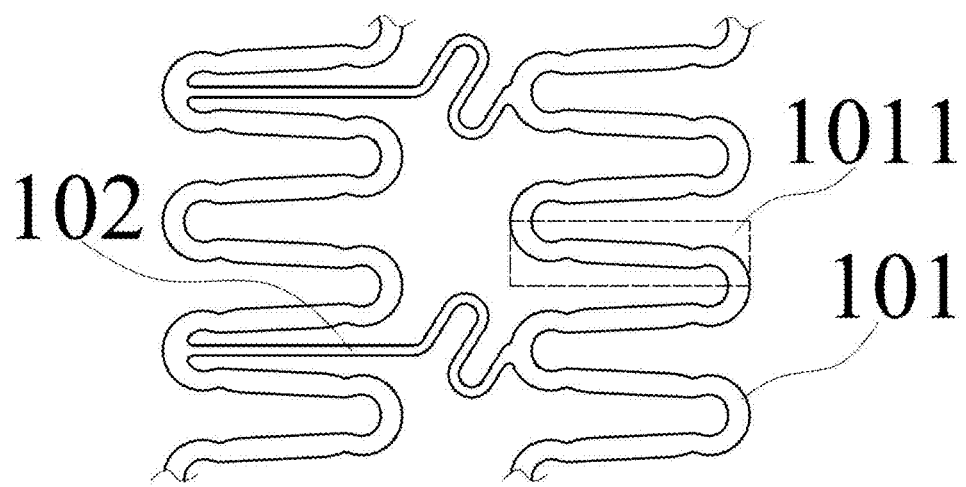
FIG. 10 is a pattern design schematic diagram of a matrix of an absorbable stent in Embodiment 11.

Referring to FIG. 10, a matrix of an absorbable peripheral vascular stent of the present embodiment is made of pure iron, and has a similar structure to that of the matrix of the absorbable coronary vessel stent of Embodiment 1. A difference lies in that: structures of wave-shaped rings 101 and connection units 102 of the stent are as shown in FIG. 10.

A prefabricated component is obtained by cutting a pure iron tube having an outer diameter of 4.2 mm and has a predetermined matrix structure has a polishing allowance of 0.055 mm. After the prefabricated component is polished into the absorbable stent 1000, the supporting strut of the stent has a wall thickness of 0.200 mm. The structure of wave 1011 is as shown in FIG. 10. The uniform strut width is 0.320 mm.

A ratio of the strut width to the wall thickness of the supporting strut is 1.60. The number A of the wave-shaped rings is 13. The number B of the connection units between the adjacent wave-shaped rings is 6. The number C of the waves included in the wave-shaped ring is 36. The included angle α0 of the supporting struts is 24 degrees. The section length L0 of the supporting strut is 1.724 mm.

When the stent is implanted into a lumen of 15.0 mm, the included angle α of the supporting struts is 96 degrees, the section length L of the supporting strut is 1.179 mm, and the absorbable matrix volume per unit vascular area of the absorbable stent is 24.0 µm.

The radial supporting strength of the absorbable peripheral vascular stent is 80 KPa, the maximum three-point bending resistance is 3.10 N, and the theoretical limit-expansion diameter of the side branch unit is 7.21 mm, so that the radial supporting strength of the absorbable peripheral vascular stent may meet the clinical applications and have good bending performance and side branch passing performance.

Embodiment 12

A matrix of an absorbable peripheral vascular stent of the present embodiment is made of nitrided iron, and has a similar structure to that of the matrix of the absorbable coronary vessel stent of Embodiment 1. A difference lies in that:

a prefabricated component is obtained by cutting a nitrided iron tube having an outer diameter of 4.6 mm and has a predetermined matrix structure has a polishing allowance of 0.550 mm. After the prefabricated component is polished into the absorbable stent 1100, the supporting strut of the stent has a wall thickness of 0.165 mm. The structure of wave is similar to that of the wave 011 of the absorbable stent of Embodiment 1. The uniform strut width is 0.280 mm.

A ratio of the strut width to the wall thickness of the supporting strut is 1.70. The number A of the wave-shaped rings is 13. The number B of the connection units between the adjacent wave-shaped rings is 6. The number C of the waves included in the wave-shaped ring is 24. The included angle α0 of the supporting struts is 23 degrees. The section length L0 of the supporting strut is 2.960 mm.

When the stent is implanted into a lumen of 16.0 mm, the included angle α of the supporting struts is 88 degrees, the section length L of the supporting strut is 2.169 mm, and the absorbable matrix volume per unit vascular area of the absorbable stent is 12.5 μm.

The radial supporting strength of the absorbable peripheral vascular stent is 60 KPa, the maximum three-point bending resistance is 4.40 N, and the theoretical limit-expansion diameter of the side branch unit is 8.11 mm, so that the radial supporting strength of the absorbable peripheral vascular stent may meet the clinical applications and have good bending performance and side branch passing performance.

Embodiment 13

A matrix of an absorbable peripheral vascular stent of the present embodiment is made of nitrided iron, and has a similar structure to that of the matrix of the absorbable coronary vessel stent of Embodiment 1. A difference lies in that:

a prefabricated component is obtained by cutting a nitrided iron tube having an outer diameter of 15.5 mm and has a predetermined matrix structure has a polishing allowance of 0.060 mm. After the prefabricated component is polished into the absorbable stent 1200, the supporting strut of the stent has a wall thickness of 0.400 mm. The structure of wave is similar to that of the wave 011 in Embodiment 1. The uniform strut width is 0.420 mm.

A ratio of the strut width to the wall thickness of the supporting strut is 1.05. The number A of the wave-shaped rings is 15. The number B of the connection units between the adjacent wave-shaped rings is 6. The number C of the waves included in the wave-shaped ring is 24. The included angle α0 of the supporting struts is 26 degrees. The section length L0 of the supporting strut is 8.788 mm.

When the stent is implanted into a lumen of 40.0 mm, the included angle α of the supporting struts is 71 degrees, the section length L of the supporting strut is 7.341 mm, and the absorbable matrix volume per unit vascular area of the absorbable stent is 40.0 μm.

The radial supporting strength of the absorbable peripheral vascular stent is 55 KPa, the maximum three-point bending resistance is 5.10 N, and the theoretical limit-expansion diameter of the side branch unit is 23.41 mm, so that the radial supporting strength of the absorbable peripheral vascular stent may meet the clinical applications and have good bending performance and side branch passing performance.

Embodiment 14

Figure 12:
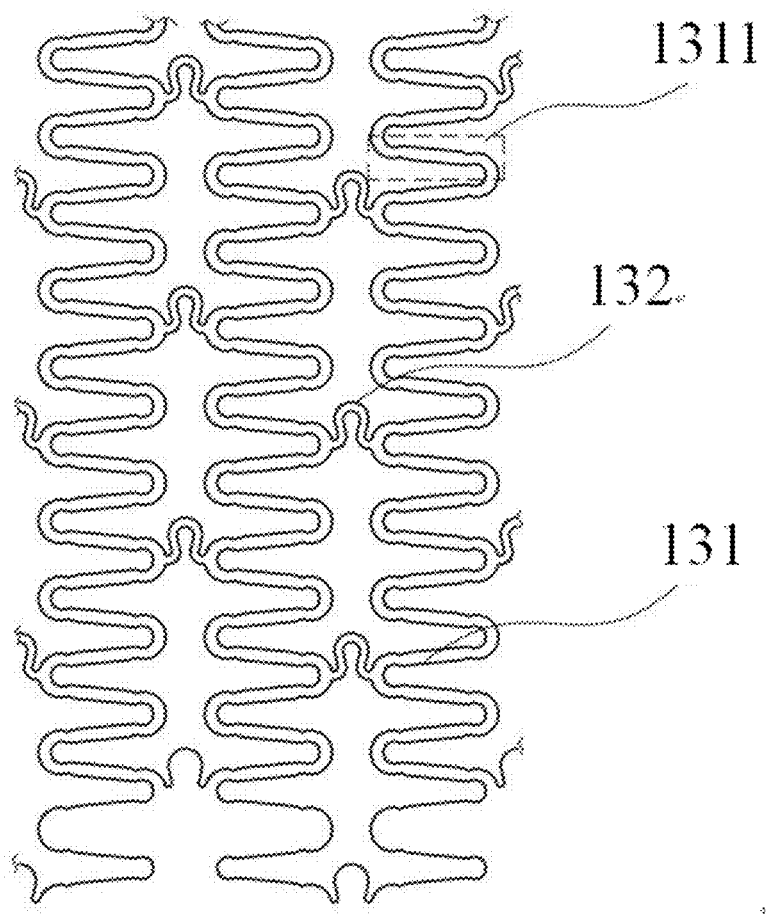
FIG. 12 is a pattern design schematic diagram of a matrix of an absorbable stent in Embodiment 14.

Referring to FIG. 12, a matrix of an absorbable coronary vessel stent of the present embodiment is made of nitrided iron, and has a similar structure to that of the matrix of the absorbable coronary vessel stent of Embodiment 1. A difference lies in that:

a prefabricated component is obtained by cutting a nitrided iron tube having an outer diameter of 1.6 mm and has a predetermined matrix structure has a polishing allowance of 0.030 mm. After the prefabricated component is polished into the absorbable stent, the supporting strut of the stent has a wall thickness of 0.060 mm. The structure of wave 1311 is as shown in FIG. 12. The supporting strut 131 is partially widened and has a strut width of [0.080, 0.094] mm.

A ratio of the strut width to the wall thickness of the supporting strut is [1.33, 1.57]. The number A of the wave-shaped rings is 32. The number B of the connection units 132 between the adjacent wave-shaped rings is 3. The number C of the waves included in the wave-shaped ring is 18. The included angle α0 of the supporting struts is 34 degrees. The section length L0 of the supporting strut is 0.923 mm.

When the stent is implanted into a lumen of 4.0 mm, the included angle α of the supporting struts is 93 degrees, the section length L of the supporting strut is 0.663 mm, and the absorbable matrix volume per unit vascular area of the absorbable stent is 6.3 μm.

The radial supporting strength of the absorbable coronary vessel stent is 110 KPa, the maximum three-point bending resistance is 0.25 N, and the theoretical limit-expansion diameter of the side branch unit is 4.17 mm, so that the radial supporting strength of the absorbable coronary vessel stent may meet the clinical applications and have good bending performance and side branch passing performance.

Contrast 1

A matrix of an absorbable coronary vessel stent of the present embodiment is made of nitrided iron, and has a similar structure to that of the matrix of the absorbable coronary vessel stent of Embodiment 2. A difference lies in that:

the supporting struts of the stent has a smaller included angle $α_0$ of 25 degrees and a greater section length $L_0$ of 1.417 mm.

When the stent is implanted into a lumen of 3.0 mm, the included angle α of the supporting struts is 48 degrees, the section length L is 1.323 mm, and the absorbable matrix volume per unit vascular area of the absorbable coronary vessel stent is 11.3 μm.

The radial supporting strength of the absorbable coronary vessel stent is 85 KPa, which is lower than that of the absorbable coronary vessel stent of Embodiment 2, and the absorbable matrix volume per unit vascular area of the absorbable coronary vessel stent is larger.

Contrast 2

A matrix of an absorbable coronary vessel stent of the present embodiment is made of nitrided iron, and has a similar structure to that of the matrix of the absorbable coronary vessel stent of Embodiment 2. A difference lies in that:

the supporting strut of the absorbable coronary vessel stent of the present embodiment has a wall thickness of 0.075 mm and a uniform strut width of 0.07 mm. A ratio of the strut width to the wall thickness of the supporting strut is 0.93.

When the stent is implanted into a lumen of 3.0 mm, the included angle α of the supporting struts is 83 degrees, the section length L of the supporting strut is 0.667 mm, and the absorbable matrix volume per unit vascular area of the absorbable stent is 8.3 μm.

The radial supporting strength of the absorbable coronary vessel stent is 85 KPa, which is obviously lower than that of the absorbable coronary vessel stent of Embodiment 2, and the absorbable matrix volume per unit vascular area of the absorbable stent is larger.

It can be seen from all the above embodiments that through the pattern design of the absorbable stent, the absorbable stent has a smaller stent volume per unit of vascular area and enough radial supporting strength so as to meet clinical requirements. Compared with Contrast 1, Embodiment 2 is different that the supporting struts of the absorbable stent has a larger included angle and a shorter section length, so that the radial strength of the stent is higher. Compared with Contrast 2, Embodiment 2 is different that the ratio of the strut width to the wall thickness is larger, so that the radial supporting strength of the stent is higher.

The above contents describe the embodiments of the present application in combination with the accompanying drawings, but the present application is not limited to the above-mentioned specific implementation modes. The above-mentioned specific implementation modes are merely schematic, but not restrictive. Those ordinarily skilled in the art can make many forms under the inspiration of the present application without departing from the objective of the present application and the scope protected by claims, and these forms shall all fall within the protection of the present application.

The invention claimed is:

1. An absorbable stent, comprising: an absorbable matrix, the matrix comprising a plurality of wave-shaped rings arrayed axially; two adjacent wave-shaped rings in the plurality of wave-shaped rings are connected by a connection unit; each wave-shaped ring comprises a plurality of circumferentially arrayed waves; each wave comprises a peak, a valley, and a supporting strut connecting the peak with the valley; two adjacent wave-shaped rings in the plurality of wave-shaped rings and the connection units form a closed side branch unit; and the absorbable matrix volume per unit vascular area is in the range of 4 μm to 40 μm;

wherein, when the matrix is expanded to a rated diameter, an included angle α of the supporting struts is in the range of 70 degrees to 100 degrees;

wherein a ratio of a strut width to a wall thickness of each supporting strut is in the range of 1 to 2;

wherein, when the rated diameter of the matrix is in the range of 1 mm to 5 mm the section length L of each supporting strut is in the range of 0.5 mm to 0.8 mm and the matrix volume per unit vascular area is in the range of 4 μm to 13 μm;

wherein, when the rated diameter of the matrix is in the range of 5 mm to 15 mm the section length L of each supporting strut is in the range of 0.9 mm to 2.0 mm and the matrix volume per unit vascular area is in the range of 8 μm to 25 μm;

wherein, when the rated diameter of the matrix is in the range of 15 mm to 40 mm the section length L of each supporting strut is in the range of 1.8 mm to 8 mm and the matrix volume per unit vascular area is in the range of 11 μm to 40 μm; and wherein a fillet is formed on the supporting strut, in cross-section of the supporting strut.

2. The absorbable stent according to claim 1, wherein the ratio of a strut width to a wall thickness of each supporting strut is in the range of 1.45 to 1.8.

3. The absorbable stent according to claim 1, wherein when the rated diameter of the matrix is in the range of 1 mm to 5 mm, the matrix volume per unit vascular area is in the range of 4 μm to 7.5 μm.

4. The absorbable stent according to claim 1, wherein when the rated diameter of the matrix is in the range of 5 mm to 15 mm, the matrix volume per unit vascular area is in the range of 8 μm to 15 μm.

5. The absorbable stent according to claim 1, wherein when the rated diameter of the matrix is in the range of 15 mm to 40 mm, the matrix volume per unit vascular area is in the range of 11 μm to 26 μm.

6. The absorbable stent according to claim 1, wherein a wall thickness of the matrix is in the range of 0.02 mm to 0.30 mm.

7. The absorbable stent according to claim 6, wherein when the rated diameter of the matrix is in the range of 1 mm to 5 mm, the wall thickness of the matrix is in the range of 0.03 mm to 0.12 mm.

8. The absorbable stent according to claim 6, wherein when the rated diameter of the matrix is in the range of 5 mm to 15 mm, the wall thickness of the matrix is in the range of 0.06 mm to 0.20 mm.

9. The absorbable stent according to claim 6, wherein when the rated diameter of the matrix is in the range of 15 mm to 40 mm, the wall thickness of the matrix is in the range of 0.13 mm to 0.26 mm.

10. The absorbable stent according to claim 1, wherein a radial supporting strength of the absorbable stent is not less than 55 kPa.

11. The absorbable stent according to claim 1, wherein the matrix is made of nitride iron.

12. The absorbable stent according to claim 1, wherein the connection unit is one of: a dot shape, a strut shape, an S shape, a Q shape, and an n shape.

* * * * *